United States Patent
Ischdonat et al.

(10) Patent No.: US 7,482,590 B2
(45) Date of Patent: Jan. 27, 2009

(54) METHOD FOR DETERMINING THE COATING QUANTITY ON A MATERIAL WEB

(75) Inventors: Thomas Ischdonat, Bachhagel (DE); Pekka M. Typpo, Cupertino, CA (US)

(73) Assignee: Voith Patent GmbH, Heidenheim (DE)

( * ) Notice: Subject to any disclaimer, the term of this patent is extended or adjusted under 35 U.S.C. 154(b) by 9 days.

(21) Appl. No.: 11/613,593

(22) Filed: Dec. 20, 2006

(65) Prior Publication Data

US 2008/0149836 A1 Jun. 26, 2008

(51) Int. Cl.
*G01J 5/02* (2006.01)
(52) U.S. Cl. .................................................. 250/339.1
(58) Field of Classification Search ............ 250/339.01, 250/339.02, 339.03, 339.04, 339.05, 339.06, 250/339.07, 339.08, 339.09, 339.1, 339.11, 250/339.12, 339.13, 339.14
See application file for complete search history.

(56) References Cited

U.S. PATENT DOCUMENTS

| | | | | |
|---|---|---|---|---|
| 4,957,770 A | * | 9/1990 | Howarth | 427/9 |
| 4,965,452 A | * | 10/1990 | Sturm | 250/339.11 |
| 5,338,361 A | | 8/1994 | Anderson et al. | 118/689 |
| 5,455,422 A | * | 10/1995 | Anderson et al. | 250/341.1 |
| 6,074,483 A | * | 6/2000 | Belotserkovsky et al. | 118/665 |
| 6,627,043 B1 | * | 9/2003 | Mantyla | 162/198 |
| 6,717,148 B2 | * | 4/2004 | Kansakoski et al. | 250/339.11 |

FOREIGN PATENT DOCUMENTS

EP 0882945 5/1998

* cited by examiner

*Primary Examiner*—David P Porta
*Assistant Examiner*—Kiho Kim
(74) *Attorney, Agent, or Firm*—Taylor & Aust, P.C.

(57) ABSTRACT

A method for determining the quantity of coating applied to a material web includes directing radiation onto the material web coated with the coating, interacting the radiation with the coating, determining, using a measurement signal produced using the detected radiation, the quantity of the coating on and/or in the material web, and detecting the radiation, after its interaction, in various frequency bands to produce a specific measurement signal for each frequency band. The frequency bands include a frequency common to all frequency bands. The frequency bands are selected such that, with any given quantity of the applied coating, at least one of the specific measurement signals varies more with the structure of the applied coating than another of the specific measurement signals. The specific measurement signals of the various frequency bands are mathematically linked with each other to determine the quantity of the coating.

23 Claims, 3 Drawing Sheets

METHOD FOR DETERMINING THE COATING QUANTITY ON A MATERIAL WEB

BACKGROUND OF THE INVENTION

1. Field of the Invention

This invention relates to a method for determining the quantity of a coating applied to a material web, in particular a fibrous web. Also, the invention relates to a method for controlling the quantity of a coating applied to a material web. In addition, the invention relates to an apparatus for applying a coating to a material web.

2. Description of the Related Art

Goods interact with the environment as a rule only with their surface. Hence, products such as foils or papers and the like are often coated nowadays.

Papers are finished in this case in a coating process in order to influence their functionality for example. Thermal papers and copy papers can be cited as examples in this connection. However, more and more papers are being coated in order to improve the printability of the paper. For example, papers for printing newspapers and magazines are coated in a coating process, thus giving rise to papers suitable for mass printing such as LWC paper for example.

The quantity of coating applied is decisive in this case for the quality of such papers. Hence, a certain minimum coating quantity on the paper for example must be observed. However, for the cost-effective and hence economical production of such papers it is also imperative for the coating quantity not to exceed certain maximum limits.

In the prior art, various techniques for determining the coating quantity, also referred to as coating weight, are in use today.

For example, the coating weight can be determined from the difference between the gsm substance before and after the coating process.

However, with the method mentioned it is possible to determine only the total coating weight, meaning the sum of the coating weight resulting from the coating of the top side and the bottom side. This is a disadvantage in particular when the coating is applied simultaneously to both sides. If the coating is applied first to the one side of the web and subsequently to the other side of the web, then the coating weight has to be measured after each application pass, which requires two measuring devices.

Mention must also be made of spectroscopic methods with which a reference signal and a measurement signal of a principal component are compared spectrally with each other, the underlying physical approach being based on Lambert Beer's law. The principal component used is kaolin, latex or $CaCO_3$ for example. Using the spectroscopic method it is possible as a rule to determine the coating weight separately for each side.

Such a method is described in EP 0 882 945 for example.

A disadvantage of these methods is, on the one hand, that the concentration of the principal component has to be sufficiently high and, on the other hand, that Lambert Beer's law presupposes a homogeneous and non-diffusing sample. In reality, however, there are diffusing particles in the sample to be measured, so the accuracy of this method is often unsatisfactory.

Methods which try to circumvent the above mentioned disadvantages use high-resolution laser spectrometry. These methods are complex and cost-intensive however. Furthermore, high-resolution laser spectrometers are sensitive and unsuitable for use in adverse conditions such as exist in the area of a paper machine.

What is needed in the art is a method of the type initially referred to, with which the described disadvantages no longer arise.

SUMMARY OF THE INVENTION

Disclosed according to the invention is a method for determining the quantity of a coating applied to a material web, in particular a fibrous web, with which radiation is directed onto the material web coated with the coating and with which the radiation interacts at least with the coating. With this method, at least a fraction of the radiation that has interacted with the coating is detected in order to determine, on the basis of at least one measurement signal produced by way of the detected radiation, the quantity of the coating on and if necessary in the material web.

The method is characterized in that the radiation, after its interaction, is detected in various frequency bands in order to produce a specific measurement signal for each frequency band, wherein the frequency bands include at least one frequency common to all frequency bands and the frequency bands are selected such that, given the same quantity of applied coating, at least one of the specific measurement signals varies more with the structure of the applied coating than another of the specific measurement signals. The method is also characterized in that the specific measurement signals of the various frequency bands are mathematically linked with each other in order to determine the quantity of the coating.

Here it should be noted that the various frequency bands of the radiation can be produced before or after its interaction with at least the coating.

During the interaction of the radiation with the coating and if necessary the material web, the radiation fraction obtained by way of the interaction is produced as the result of numerous influencing factors such as absorption or diffusion for example.

In this case the absorption is defined essentially by the quantity of coating applied, whereas the diffusion is influenced essentially by the inner structure and/or the surface structure due to graining, grain limits, surface roughness and the like. If only one measurement signal is generated, then it is impossible to separate these different influencing factors from each other, as the result of which it is impossible to exactly determine the coating weight on the basis of the measurement signal.

The method of the invention is based on the idea of producing several measurement signals that have at least one frequency in common and which, for a given coating quantity, are differently sensitive with regard to the structure of the applied coating. Given the same coating quantity, the different influencing factors result in a different shape of measurement signal and, consequently, different mean values of the various specific measurement signals, hence the coating weight can be exactly determined through a mathematical logic operation of the specific measurement signals of the various frequency bands in spite of the different influencing factors.

In the coating materials used today to coat paper, more and more $CaCO_3$ is used. During the interaction of the radiation with the coating, the radiation is partly absorbed at certain frequencies, wherein the degree of absorption is a measure of the coating quantity applied. Therefore, the common frequency is selected preferably such that the radiation is at least partly absorbed during interaction with the coating.

Another variable with an influence on the interacted signal is the diffusion fraction, wherein the diffusion fraction of the signal is not influenced by the applied coating quantity but by the size and shape of the particles in the coating.

Hence the radiation received is more or less intensively absorbed during its interaction with the coating depending on the frequency. Furthermore, the radiation is diffusely reflected by the particles in the coating.

The specific measurement signal of each frequency band is therefore a function of the absorption and the diffusion of the radiation received.

Tests have revealed that the shape of the measurement signal as a function of the frequency is defined by the grain size of the diffusing particles. Hence it is possible with the method of the invention to clearly determine the applied coating quantity in spite of the structure information contained in the measurement signals and conditional on diffusion.

Because $CaCO_3$ is absorbed in the infrared spectral range, an embodiment of the invention provides for the at least one common frequency to lie in the infrared spectral range, in particular at a wave length of approx. 4 µm.

The specific measurement signal of each frequency band can include a fraction of the radiation reflected due to interaction. In this case the reflection is essentially diffuse. Alternatively, the specific measurement signal of each frequency band can include a fraction of the radiation transmitted due to the interaction, wherein the transmission is essentially diffuse.

The frequency bands include one frequency band common to all frequency bands.

According to another embodiment of the invention, all frequency bands are of different size, wherein the respectively smaller frequency band is arranged entirely within the respectively larger frequency bands.

A concrete embodiment of the method of the invention provides in this case for the smallest of the frequency bands to be the common frequency band, wherein in particular the smallest of the frequency bands is selected such that its specific measurement signal has the greatest dependency, in relation to the other specific measurement signals, on the structure of the applied coating and wherein in particular the largest of the frequency bands is selected such that its specific signal, in relation to the other specific measurement signals, has the smallest dependency on the structure of the applied coating.

In this connection it is possible, for example, for the frequency bands to all have one common center frequency.

If the size of the particles in the coating changes, then not only the shape of the specific measurement signals measured in reflection for example changes, but also the respective mean values of the intensity. An embodiment of the invention provides accordingly for each of the specific measurement signals to be formed proportionally to the mean value of the intensity of the interacted radiation over the respective frequency band.

A concrete possibility for the mathematical logic operation for determining the applied coating quantity M looks in this connection as follows:

$$[S3/(S2-S1)]-1 \sim M$$

where

S3 is the specific measurement signal proportional to the mean value of the intensity over the smallest of the frequency ranges, which varies most with the structure of the applied coating, S1 is the specific measurement signal proportional to the mean value of the intensity over the largest of the frequency ranges, which varies least with the structure of the applied coating, S2 is the specific measurement signal proportional to the mean value of the intensity over the middle one of the frequency ranges, and where the respectively smaller frequency band is arranged entirely within the respectively larger frequency bands and the smallest of the frequency bands forms the common frequency band.

In this case the frequency bands can be selected simply by way of bandpass filters for example.

Disclosed according to another aspect of the invention is a method for controlling the quantity of a coating to be applied to a material web with the following steps: determination, using the previously described method, of the quantity of the coating which was applied to a section of the material web in an application step; comparison of the determined actual value of the coating quantity with a set-point of the coating quantity; and actuation of at least one actuating element on the basis of the comparison between the set-point value and the actual value, in order to influence the quantity of the coating which is applied to a section of the material web not yet coated with the application step.

Using the method of the invention it is thus possible to control the coating quantity during production.

Also disclosed according to the present invention is an apparatus for applying a coating to a moving material web, said apparatus including an applicator with at least one actuating element for controlling the coating quantity and at least one measuring device that is suitable for performing the method of the invention, wherein the measuring device is fitted downstream from the applicator in the web running direction, and a computer for determining the difference between the actual value and the set-point value of the coating and for calculating the actuating signals for the applicator.

One measuring device suitable for performing the method for determining the coating quantity is fitted respectively upstream and downstream from the applicator in the web running direction, wherein the apparatus includes a computer for determining the difference signal of the two measuring devices and the actual value for the coating resulting therefrom.

In addition it can make sense for the apparatus to include several applicators and for the measuring device to be suitable in particular for determining the coating quantity applied respectively to the top side and the bottom side of the material web independently of each other.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate one embodiment of the invention, and such exemplifications are not to be construed as limiting the scope of the invention in any manner.

DETAILED DESCRIPTION OF THE INVENTION

Figure 1:
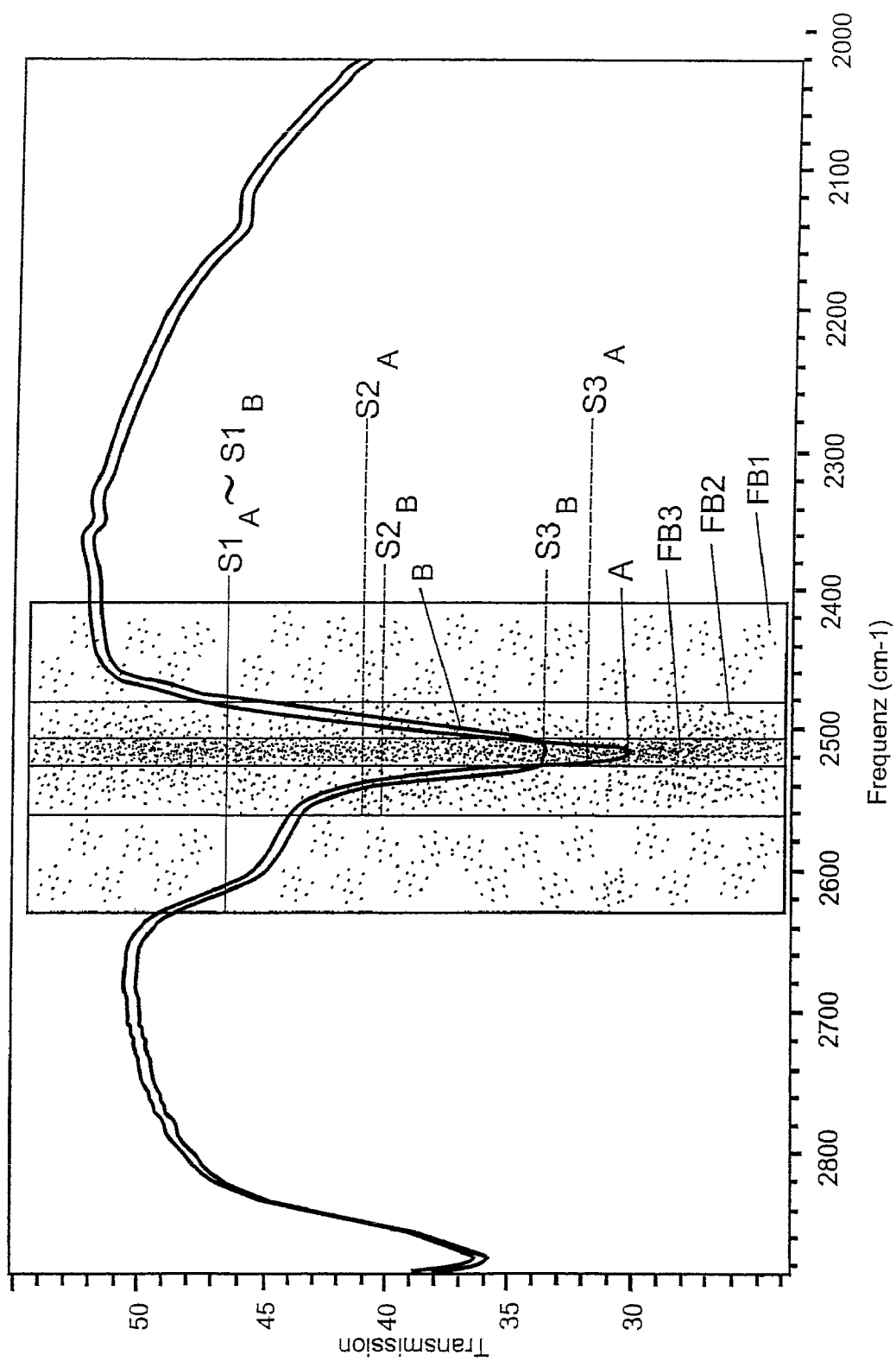
FIG. 1 shows various transmission spectra after the interaction of IR radiation with the coating of a paper web.

Referring now to the drawings, and more particularly to FIG. 1, there is shown two different transmission spectra such as result from the interaction of radiation in the frequency range between 2000 cm-1 and 2900 cm-1 with a coating applied to a paper web.

Spectrum A results in this case from a coating with particles having a small grain size, whereas spectrum B results from a coating with larger particles.

With the method of the invention, the interacted radiation is detected in various frequency bands FB1, FB2 and FB3, as the result of which a specific measurement signal, formed using the mean value of the intensity over the respective frequency band, is produced for each frequency band, namely S1 for FB1, S2 for FB2 and S3 for FB3. In this case FB1 extends from 2440 $cm^{-1}$ to 2600 $cm^{-1}$, FB2 from 2480 $cm^{-1}$ to 2560 $cm^{-1}$ and FB3 from 2500 $cm^{-1}$ to 2520 $cm^{-1}$ so that all frequency bands FB1 to FB3 include one frequency section that is common to all frequency bands and extends over the frequency band FB3.

Entered in FIG. 1 are the mean values of the intensity $S1_A$ to $S3_A$ for the frequency spectrum A and the mean values of the intensity $S1_B$ to $S3_B$ for the frequency spectrum B. It is evident that the specific measurement signals $S3_A$, $S3_B$ depend greatly on the structure of the applied coating, whereas the specific measurement signals $S1_A$, $S1_B$ are practically independent of the structure.

Using the inventive mathematical combination of the specific measurement signals, even fluctuations of the illumination source used to emit the radiation for interaction with the coating are compensated.

Furthermore, all the frequency bands FB1 to FB3 are of different size, wherein the respectively smaller frequency band is arranged entirely within the respectively larger frequency bands. For example, the frequency band FB3 is arranged within the two larger frequency bands FB1 and FB2, the same as the frequency band FB2 is arranged within the larger frequency band FB1, wherein the smallest frequency band FB3 forms the common frequency band. As is evident from FIG. 1, all the frequency bands have a common center frequency that lies at approx. 2510 $cm^{-1}$.

According to the method of the invention, the specific measurement signals Si to S3 of the various frequency bands FB1 to FB3 are mathematically linked with each other to determine the quantity M of the coating so that the coating quantity can clearly be presented as a function of the specific measurement signals S1 to S3. In this case the specific measurement signals are formed respectively by the mean value of the intensity of the interacted radiation over the respective frequency band.

Hence: M=Function(S1, S2, S3)

Figure 2:
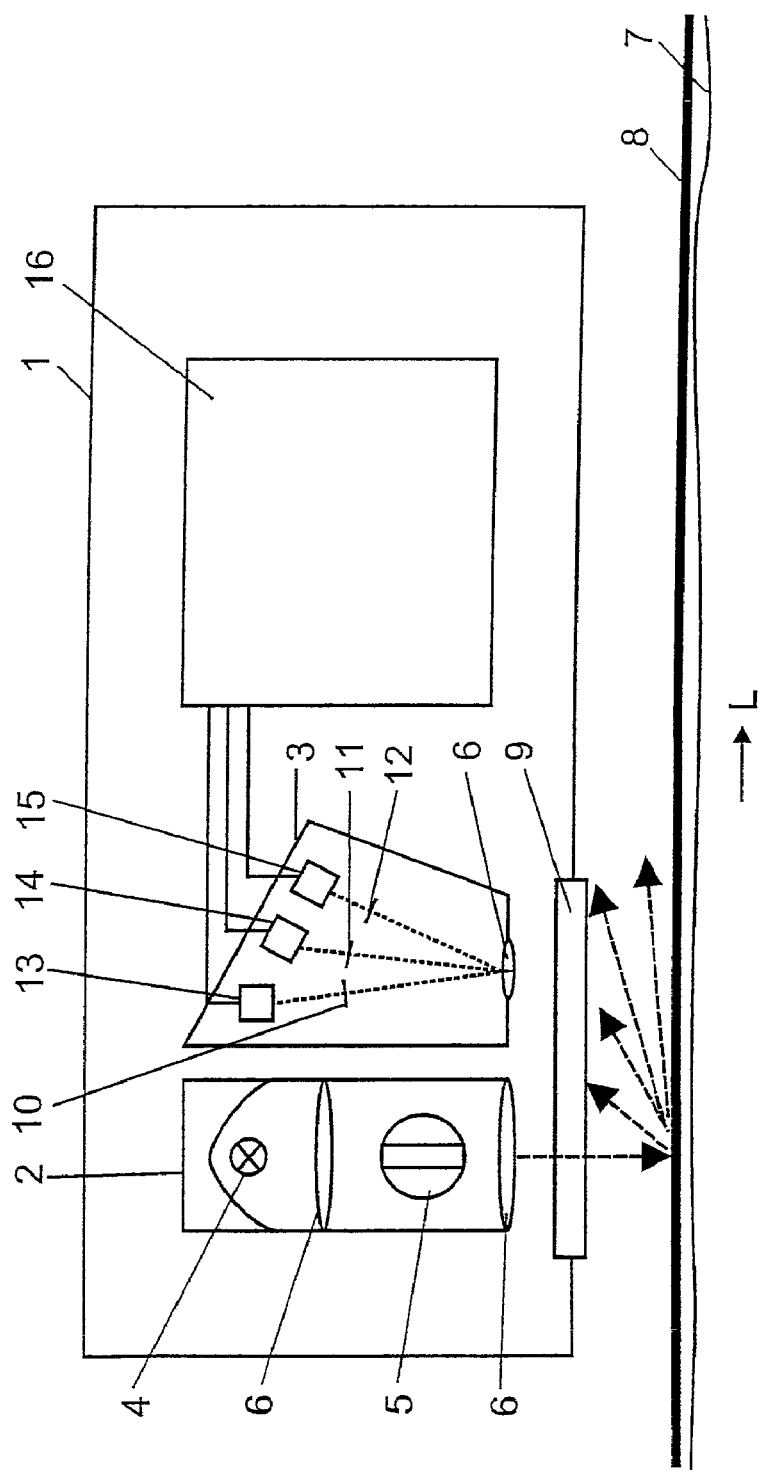
FIG. 2 shows a sensor that is suitable for performing the method of the invention.

FIG. 2 shows, in a schematic representation, a sensor 1 with which the inventive method can be performed. The sensor 1 includes an illumination unit 2 and a detector unit 3.

Arranged in the illumination unit 2 is an infrared radiation source 4 whose emitted radiation is chopped by a chopper unit 5. In addition the illumination unit 2 includes a number of lenses 6, by way of which the radiation is directed onto a paper web 7 with a coating 8 running in a running direction L. Furthermore, the sensor 1 includes a window 9, through which the radiation directed from the illumination unit 2 onto the paper web 7 exits from the sensor 1 and through which the radiation fraction that has interacted with at least the coating 8 enters into the sensor 1 in order to get into the detector unit 3.

In the case of the illustrated sensor 1, the illumination unit 2 and the detector unit 3 are both arranged on the same side of the paper web 7. Hence it is possible with the sensor 1 to measure in reflection the absorption of the radiation during interaction with at least the coating 8, wherein the reflection is essentially diffuse due to diffusion of the radiation on particles in the coating.

The diffusely reflected radiation passes through the window 9 and through one or more of the lenses 6 into the detector unit 3 and is split into various rays. Then the various rays pass respectively through different bandpass filters 10, 11 and 12.

The bandpass filters 10 to 12 are constructed such that the frequency bands produced by them include a frequency range common to all frequency bands and such that all frequency bands are of different size, wherein the respectively smaller frequency band is arranged entirely within the respectively larger frequency bands. In addition, the frequency bands all have a common center frequency. The thus constructed bandpass filters 10 to 12 produce, for example, the frequency bands FB1 to FB3 described in FIG. 1.

As the result of the radiation passing through the bandpass filters 10 to 12, the respectively filtered radiation reaches the detectors 13 to 15, which are assigned to the respective bandpass filters 10 to 12 and in which a specific measurement signal is produced for each of the frequency bands. The specific measurement signals are fed to a signal processing unit 16 which mathematically links the measurement signals with each other in order to determine the weight of the applied coating 8.

Figure 3:
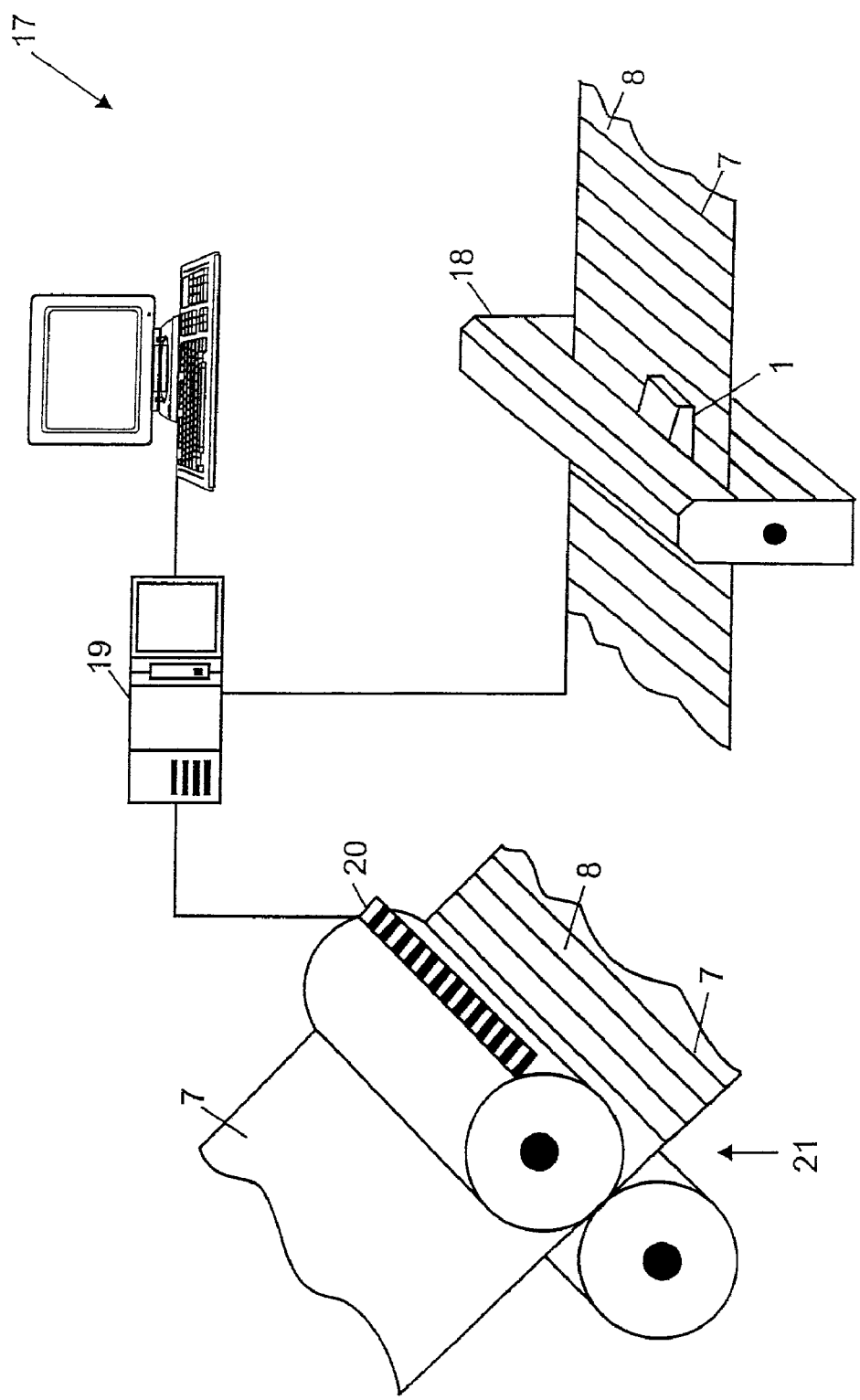
FIG. 3 shows a subsection of a paper machine with a sensor and a coating applicator.

FIG. 3 shows a subsection of a paper machine 17, in which the sensor 1 for determining the coating quantity is arranged in a position where the coating 8 has already been applied to the paper web 7. The sensor 1 is traversingly mounted transverse to the paper web on a scanner 18 such that it is possible with the sensor 1 to continuously detect, in local resolution over the width of the paper web 7, the quantity of applied coating 8.

The sensor 1 sends information concerning the coating quantity to a control unit 19, which compares the actual value of the coating quantity determined in local resolution in transverse direction, for example, with a set-point value of the coating quantity. On the basis of the comparison between the set-point value and the actual value, the control unit 19 operates one or more actuating elements 20 of an applicator 21 in order to influence the quantity of coating 8 which is applied to an as yet uncoated section of the paper web 7.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for determining a quantity of a coating applied to a material web, said method comprising the steps of:
   directing radiation onto the material web coated with the coating;
   interacting said radiation at least with the coating;
   detecting at least a fraction of said radiation that has interacted with the coating, in order to determine, based on at least one measurement signal produced by detected said radiation, the quantity of the coating at least one of on and in the material web, said step of detecting further comprising detecting, after interacting with the coating, said radiation in a plurality of frequency bands in order to produce a plurality of respective specific measurement signals, said plurality of frequency bands including at least one common frequency which is common to all of said plurality of frequency bands; said plurality of frequency bands being selected such that, given a same quantity of the applied coating, at least one of said plurality of specific measurement signals varies more with a structure of the applied coating than another of said plurality of specific measurement signals so as to thereby account for, at least in part, any diffusion of said radiation caused by said structure when determining the quantity of the coating; said plurality of specific measurement signals of said plurality of frequency bands being mathematically linked with each other to determine the quantity of the coating.

2. The method according to claim 1, wherein at said common frequency said radiation is at least partly absorbed during interaction with said coating.

3. The method according to claim 1, wherein said fraction includes a fraction of said radiation reflected due to interaction, each of said plurality of specific measurement signals of each of said plurality of frequency bands produced by said fraction of said radiation reflected due to interaction.

4. The method according to claim 1, wherein said fraction includes a fraction of said radiation transmitted due to interaction, each of said plurality of specific measurement signals of each of said plurality of frequency bands produced by said fraction of said radiation transmitted due to interaction.

5. The method according to claim 1, wherein said at least one common frequency lies in an infrared spectral range.

6. The method according to claim 5, wherein said at least one common frequency lies in said infrared spectral range at a wave length of approximately 2500 cm$^{-1}$.

7. The method according to claim 1, wherein said plurality of frequency bands comprises one common frequency band which is common to all of said plurality of frequency bands.

8. The method according to claim 7, wherein all of said plurality of frequency bands are of a different size, a respectively smaller frequency band of said plurality of frequency bands arranged entirely within a plurality of respectively larger frequency bands of said plurality of frequency bands.

9. The method according to claim 8, wherein said plurality of frequency bands comprises a smallest frequency band which is said common frequency band.

10. The method according to claim 9, wherein said plurality of frequency bands comprises a largest frequency band which corresponds to a largest frequency band specific measurement signal of said plurality of specific measurement signals, said largest frequency band selected such that said largest frequency band specific measurement signal, in relation to other of said plurality of specific measurement signals, has a smallest dependency on said structure of the applied coating.

11. The method according to claim 10, said largest frequency band specific measurement signal is essentially independent of said structure of the applied coating.

12. The method according to claim 9, wherein said smallest frequency band corresponds to a smallest frequency band specific measurement signal of said plurality of specific measurement signals, said smallest frequency band selected such that said smallest frequency band specific measurement signal, in relation to other of said plurality of specific measurement signals, has a greatest dependency on said structure of the applied coating.

13. The method according to claim 9, wherein all of said plurality of frequency bands have one common center frequency.

14. The method according to claim 1, wherein each of said plurality of specific measurement signals is proportional respectively to a mean value of an intensity of an interacted radiation over respective said plurality of frequency bands.

15. The method according to claim 1, wherein said plurality of frequency bands are selected by a plurality of bandpass filters.

16. The method according to claim 1, wherein the quantity of the coating applied to the material web is continuously determined online.

17. The method according to claim 1, further including the step of measuring said radiation in an infrared wavelength range.

18. The method according to claim 1, further including the step of measuring said radiation in an infrared wavelength range to determine a moisture of the material web with the applied coating.

19. A method for controlling a quantity of a coating applied to a material web, said method comprising the steps of:
  determining the quantity of the coating which has been applied to a first section of the material web in an application step, said step of determining comprising the steps of:
    directing radiation onto the material web coated with the coating;
    interacting said radiation at least with the coating; and
    detecting at least a fraction of said radiation that has interacted with the coating, in order to determine, based on at least one measurement signal produced by detected said radiation, the quantity of the coating at least one of on and in the material web, said step of detecting further comprising detecting, after interacting with the coating, said radiation in a plurality of frequency bands in order to produce a plurality of respective specific measurement signals, said plurality of frequency bands including at least one common frequency which is common to all of said plurality of frequency bands; said plurality of frequency bands being selected such that, given a same quantity of the applied coating, at least one of said plurality of specific measurement signals varies more with a structure of the applied coating than another of said plurality of specific measurement signals so as to thereby account for, at least in part, any diffusion of said radiation caused by said structure when determining the quantity of the coating; said plurality of specific measurement signals of said plurality of frequency bands being mathematically linked with each other to determine the quantity of the coating;
  comparing a determined actual value of the coating quantity with a set-point of the coating quantity; and
  actuating at least one actuating element based on a comparison between a set-point value of the coating quantity and said actual value of the coating quantity, in order to influence the quantity of the coating which is applied to a second section of the material web not yet coated in said application step.

20. An apparatus for applying a coating to a moving material web, said apparatus comprising:
  an applicator with at least one actuating element for controlling a coating quantity of the coating;

at least one measuring device that is suitable for determining said quantity of the coating applied to a material web by:

directing radiation onto the material web coated with the coating;

interacting said radiation at least with the coating; and detecting at least a fraction of said radiation that has interacted with the coating, in order to determine, based on at least one measurement signal produced by detected said radiation, said quantity of the coating at least one of on and in the material web, detecting, after interacting with the coating, said radiation in a plurality of frequency bands in order to produce a plurality of respective specific measurement signals, said plurality of frequency bands including at least one common frequency which is common to all of said plurality of frequency bands; said plurality of frequency bands being selected such that, given a same quantity of the applied coating, at least one of said plurality of specific measurement signals varies more with a structure of the applied coating than another of said plurality of specific measurement signals so as to thereby account for, at least in part, any diffusion of said radiation caused by said structure when determining the quantity of the coating; said plurality of specific measurement signals of said plurality of frequency bands being mathematically linked with each other to determine said quantity of the coating;

wherein said measuring device is fitted downstream from said applicator in a web running direction; and a control unit for determining a difference between an actual value and a set-point value of the coating and for calculating a plurality of actuating signals for said applicator.

21. The apparatus according to claim 20, wherein said at least one measuring device includes a first measuring device and a second measuring device, said first measuring device fitted respectively upstream from said applicator, said second measuring device fitted downstream from said applicator, said control unit for determining a difference signal of said first and second measuring devices and said actual value for the coating resulting therefrom.

22. The apparatus according to claim 20, further comprising several applicators.

23. The apparatus according to claim 20, wherein said at least one measuring device is suitable for determining said coating quantity applied respectively to a top side and a bottom side of the material web independently of each other.

* * * * *